US00PP10755P

United States Patent [19]

Nagase

[11] Patent Number: Plant 10,755

[45] Date of Patent: Jan. 12, 1999

[54] VERBENA PLANT NAMED 'SUNMAREF TP-SP'

[75] Inventor: Yuki Nagase, Seki, Japan

[73] Assignee: Suntory Limited, Osaka, Japan

[21] Appl. No.: 764,734

[22] Filed: Dec. 3, 1996

[51] Int. Cl.[6] ..... A01H 5/00

[52] U.S. Cl. ..... Plt./87

[58] Field of Search ..... Plt./87

[56] References Cited

U.S. PATENT DOCUMENTS

P.P. 8,995 11/1994 Tachibana et al. ..... Plt./87
P.P. 9,014 12/1994 Tachibana et al. ..... Plt./87
P.P. 9,059 2/1995 Tachibana et al. ..... Plt./87
P.P. 9,085 3/1995 Tachibana et al. ..... Plt./87
P.P. 9,121 4/1995 Tachibana et al. ..... Plt./87
P.P. 9,411 12/1995 Tachibana et al. ..... Plt./87

*Primary Examiner*—Howard J. Locker
*Attorney, Agent, or Firm*—Burns, Doane, Swecker & Mathis, L.L.P.

[57] ABSTRACT

A new and distinct Verbena variety is provided which forms attractive medium-sized purplish pink blossoms. The plant is broad and exhibits a spreading growth habit. The blossoms are borne in abundance on spikes. The blossoming is of long duration and commonly occurs between April and November. The plant exhibits a high tolerance to rain, cold, and heat and good resistance to diseases, such as powdery mildew.

2 Drawing Sheets

BACKGROUND OF THE VARIETY

The present invention relates to a new and distinct variety of Verbena plant obtained from a crossing *Vorbena×hybrida* 'Rainbowcarpet rose' (♀) and a wild type of Verbena plant *Verbena peruviana* f. rosea. (♂) native to Brazil.

The Verbena is a very popular plant and is used for flower bedding and as a pot plant in the summer season. There are only a few varieties of the verbena plant which have a spreading growth habit, much branching, the formation of a high number of flowers in a spike and which have a high resistance to rain, heat, cold, and deseases. Accordingly, this invention was aimed at obtaining a new variety having a spreading growth habit, strong branching, the formation of a high number of flowers in a spike, high tolerance to heat, rain, drought and cold, and resistance to diseases and pests, and also having strong purplish pink flower petals.

The new variety of verbena plant according to this invention originated from crossing of 'Rainbowcarpet rose' (♀) and a wild type of verbena plant *Verbena peruviana* f. rosea. (♂) native to Brazil.

First of all, 4 seedlings were obtained from crossing *Verbena×hybrida* 'Rainbowcarpet rose' as female parent and a wild type of verbena plant (*Verbena peruviana* f. rosea) as pollen parent in the May of 1992. From this crossing 1 seedling was selected in view of the spreading growth habit and flower coloration. This seedling that was selected was propagated by the use of cuttings and was grown for evaluation during which time the botanical characteristics of the seedling was examined, using the similar variety 'Rainbowcarpet rose' for comparison, from in the spring of 1993 to in the autumn of 1994. As a result, it was concluded that this Verbena is distinguishable from any other variety whose existence is known to us, and is uniform and is stable in its characteristics. This new variety of Verbena plant was named 'SUNMAREF TP-SP'. The new variety of the present invention is botanically classified as *Verbena×hybrida.*

In the following description, the color-coding is in accordance with the Horticultural Color Chart of The Royal Horticultural Society, London, England (R.H.S. Colour Chart), and the Inter-Society color Council-Nation Bureau of Standard Color Name (I.S.C.C.-N.B.S. Color Name). A color designation based on The Japan Color Standard for Horticultural Plant (J.H.S. Color Chart) is also added for reference.

The 'Rainbowcarpet rose' used as female parent in the obtaining of this new variety 'SUNMAREF TP-SP', is bred by the Takii Seed Corp., Japan and is commercially available. Such parent was registered on Jul. 15, 1989 as No. 1953 under the Seed and Seedling Law of Japan. The 'Rainbowcarpet' series includes 'Rainbow-carpet bright purple', 'Rainbowcarpet white' and the like. The main botanical characteristics of 'Rainbow-carpet rose' are as follow.

Plant:
- *Growth habit.*—Semi-erect.
- *Plant extension.*—25–30 cm.
- *Plant height.*—20–25 cm.

Stem:
- *Diameter.*—1.7–1.9 mm.
- *Anthocyanin pigmentation.*—Absent.
- *Branching.*—Medium.
- *Subterranean stem.*—Absent.
- *Pubescence.*—Few.
- *Length of internode.*—3.0–3.5 cm.

Leaf:
- *Phyllotaxis.*—Opposite.
- *Shape of blade.*—Cordate.
- *Length.*—2.0–2.5 cm.
- *Width.*—1.5–2.0 cm.
- *Depth of incision.*—Deep.
- *Color.*—Dark green (R.H.S. 137B, JHS 3716).
- *Pubescence.*—Few.

Flower:
- *Facing direction.*—Upward.
- *Outward curvature of petal.*—Curved.
- *Diameter.*—1.2–1.7 cm.
- *Height.*—13–15 mm.
- *Color.*—Vivid purplish red (R.H.S. 57C, JHS 9707).
- *Color intensity.*—Absent.
- *Overlapping of petals.*—Opened.
- *Spike.*—25–30 mm in length; and 30–35 m m in diameter.
- *Calyx.*—0.5–1.0 cm in length.

*Anthocyanin pigmentation of calyx limb.*—Present.
*Peduncle.*—1.7–1.8 mm in thickness; and 4.0–6.0 cm in length.
*Number of flowers.*—Few (7–11).
*Reproductive organs.*—1 pistil and 5 stamens.
*Flower fragrance.*—Absent.
*Flowering duration.*—Medium.

Physiological and ecological characteristics: Moderate tolerance to heat, cold, and pests and low resistance to diseases.

The pollen parent used in the obtaining of this new variety 'SUNMAREF TP-SP' was a wild type of Verbena native to South Brazil which introduced to Japan in 1991 and *Verbena peruviana* f. rosea. This wild type of verbena plant is presently maintained at the Plant Biotechnology Laboratory of SUNTORY Ltd., residing at 863-1, Aza-Iketani, Oomori-cho, Youkaiti-shi, Shiga-ken, Japan. The main botanical characteristics of this pollen parent are as follows.

Plant:
*Growth habit.*—Slightly erect and spreading.
*Plant extension.*—130–180 cm.
*Plant height.*—5–8 cm.

Stem:
*Diameter.*—2.0–3.0 m m.
*Anthocyanin pigmentation.*—Present.
*Branching.*—Medium.
*Subterranean stem.*—Absent.
*Pubescence.*—Medium. .
*Length of internode.*—4.0–5.0 cm.

Leaf:
*Phyllotaxis.*—Opposite.
*Shape of blade.*—Narrow lanceolate.
*Length.*—3.0–4.0 cm.
*Width.*—2.0–2.5 cm.
*Depth of incision.*—Shallow.
*Color.*—Moderate olive green (R.H.S. 146A, JHS 3509).
*Pubescence.*—Few.

Flower:
*Facing direction.*—Upward.
*Outward curvature of petal.*—Slightly curved.
*Diameter.*—1.7–2.0 cm.
*Height.*—15–20 m m.
*Color.*—Yellowish white (R.H.S. 159D, JHS 1901).
*Color intensity.*—Absent.
*Overlapping of petals.*—Separate.
*Spike.*—30–40 m m in length; and 40–50 m m in diameter.
*Calyx.*—1.0 cm in length.
*Anthocyanin pigmentation of calyx limb.*—Present.
*Peduncle.*—1–2 m m in thickness; and 5.0 cm in length.
*Number of flowers.*—Abundant (Commonly 13 to 15).
*Reproductive organs.*—1 pistill and 5 stamens.
*Flower fragrance.*—Absent.
*Flowering duration.*—Short.

Physiological and ecological characteristics: High resistance to diseases and pests, high tolerance to heat and moderate tolerance to cold.

This new variety of verbena plant 'SUNMAREF TP-SP ' was asexually reproduced by the use of cuttings at the aformentioned the Plant Biotechnology Laboratory of SUNTORY Ltd., residing at 863–1 Aza - Iketani, Oomori-cho, Youkaiti-shi, Shiga-ken, Japan, and the homogeneity and stability thereof were confirmed.

SUMMARY OF THE VARIETY

This new variety of verbena plant has spreading growth habit with long stems A broad plant is formed. The plant has abundant branching and forms a large number of flowers in a spike, and great profusion of blooms. The Blooming period is April to November and flowering duration is long, and the whole bush remains in bloom for considerable period of time. The flower size is medium and the petal coloration of flower is strong purplish pink. The plant is highly tolerant to cold, heat, rain and drought and exhibits a high resistance to pests and diseases, particularly powdery mildew.

DESCRIPTION OF THE VARIETY

Figure 1:
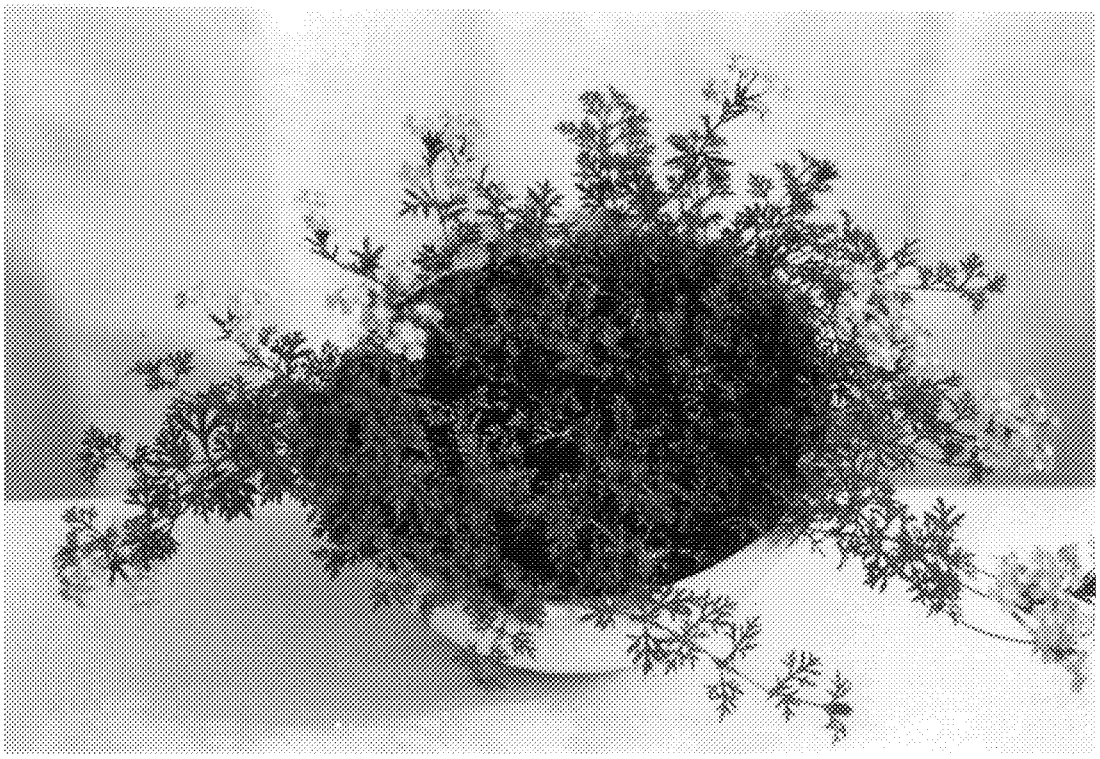
FIG. 1 is photograph giving a partial view of the new variety of verbena plant when planted in a flower pot.
Figure 2:
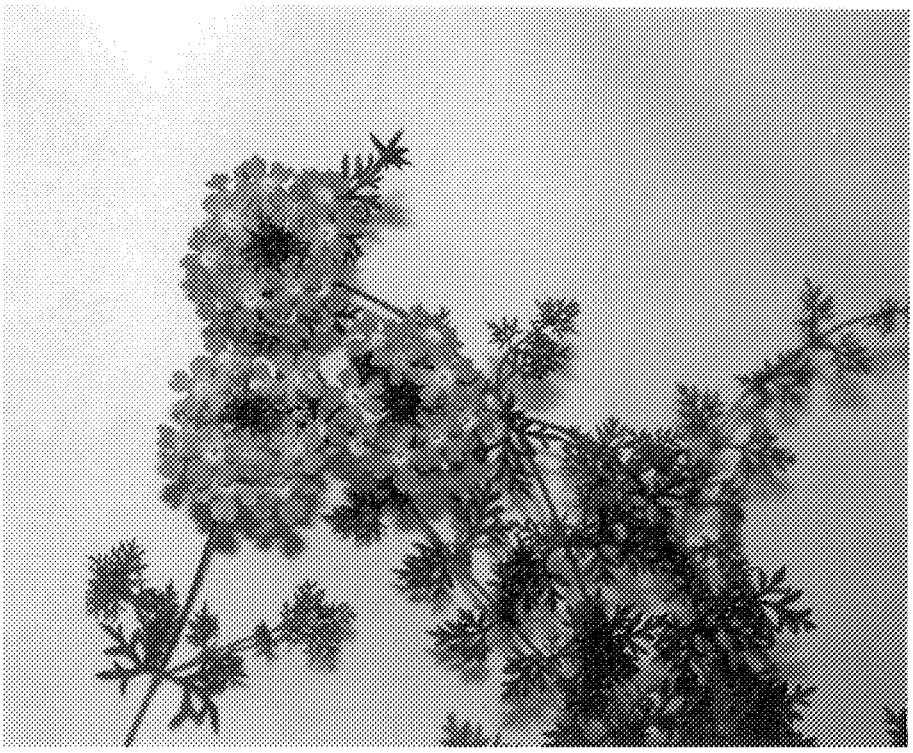
FIG.2 is a photograph of flowers of the new variety of verbena plant.

The botanical characteristics of the new and distinct variety of verbena plant, 'SUNMAREF TP-SP' are as follows.

Plant:
*Growth habit.*—Spreading.
*Plant extension.*—Approximately 80–100 cm.
*Plant height.*—Approximately 10–20 cm.
*Growth.*—Very vigorous with abundant branching and with a great profusion of blooms. The whole bush remains in bloom for considerable period of time.

Stem:
*Diameter.*—2.0–3.0 m m.
*Anthocyanin pigmentation.*—Absent.
*Branching.*—Abundant.
*Subterranean stem.*—Absent. But when the stems contact the surface of soil, the nodes may take root into the ground.
*Pubescence.*—Medium.
*Length of internode.*—Approximately 3.0–4.0 cm.

Leaf:
*Phyllotaxis*—Opposite.
*Shape of blade.*—Cordate.
*Length.*—Approximately 1.0–3.0 cm.
*Width.*—Approximately 0.5–3.0 cm.
*Depth of incision.*—Deep.
*Color.*—Dark yellow green (R.H.S. 146A, JHS 3308).
*Pubescence.*—Medium.

Flower:
*Facing direction.*—Upward.
*Outward curvature of petal.*—Slightly curved.
*Diameter.*—Approximately 1.0–1.5 cm.
*Height.*—Approximately 15–20 m m.
*Color.*—Strong purplish pink (R.H.S. 61D, JHS 9505) on the upper surface, and more purple on the under surface (R.H.S. 75A, JHS 8904). The throat coloration is pale purplish pink (R.H.S. 75, D, J H S 8902). The eye coloration is purplish white (R.H.S. 76D, JHS 8901).
*Color intensity.*—Absent.
*Overlapping of petals.*—Opened.
*Spike.*—Approximately 30–40 m m in length; and approximately 30–50 m m in diameter.

*Calyx.*—Approximately 0.5–1.0 cm in length.

*Anthocyanin pigmentation of calyx limb.*—Present.

*Peduncle.*—1 mm in thickness; and 4.0–5.0 cm in length.

*Number of flowers.*—Numerous (Approximately 10–14)

*Reproductive organs.*—pistil and 5 stamens.

*Flower fragrance.*—Absent.

*Flowering duration.*—Long.

Physiological and ecological characteristics: High resistance to diseases and pests, particularly powdery mildew. High tolerance to heat, cold, rain and drought exhibited. When provided with sufficient nutrition, the new variety of the present invention has been found to overwinter well when encountering temperatures as low as approximately – 5° C. However, the plant has been harmed when the temperatures encounted are as low as approximately –° C.

This new variety of Verbena plant is most suitable for growing as flower bedding and as a pot plant in planters, and is further is particulary well suited for growing as a ground cover. Upon self-pollination viable seed forms on the plant of the new variety of the present invention. However, such seed does not form plants identical to the new variety since the new variety is a $F_1$ hybrid.

Pinching of the blossoms is not necessary to ensure continued blooming. It is found that such pinching will increase the number of blooms that are formed.

When the new variety of the present invention is compared to the 'Sunmaref TP-L' variety (U.S. Plant Pat. No. 9,121), it is found that the upper petal surface is strong purplish pink (JHS 9505) for the new variety and vivid purple (JHS No. 8605) for the 'Sunmaref TP-L' variety. Also, the flower eye coloration of the new variety is purplish white (JHS 8901) for the new variety and pale purple (JHS 8302) for the 'Sunmaref TP-L' variety.

The plant of this new variety, 'SUNMAREF TP-SP' is presently planted and maintained at the Plant Biotechnology Laboratory of SUNTORY Ltd., residing at 863-1 Aza-Iketani, Oomori-cho, Youkaiti-shi, Shiga-gun, Japan.

I claim:

1. A new and distinct variety of verbena plant having the following combination of characteristics:

(a) exhibits a spreading growth habit with long stems,
(b) forms in abundance on spikes attractive medium-sized purplish pink blossoms over an extended period of time,
(c) exhibits a high tolerance to rain, cold and heat, and
(d) exhibits good resistance to powdery mildew;
substantially as illustrated and described.

* * * * *